US00PP19953P2

(12) United States Plant Patent
Kools

(10) Patent No.: US PP19,953 P2
(45) Date of Patent: Apr. 21, 2009

(54) JUNIPER PLANT NAMED 'HULSDONK YELLOW'

(50) Latin Name: *Juniperus pingii*
Varietal Denomination: Hulsdonk Yellow

(75) Inventor: Cornelius Petrus Franciscus Kools, Deurne (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 12/151,752

(22) Filed: May 8, 2008

(51) Int. Cl.
*A01H 5/00* (2006.01)

(52) U.S. Cl. ..... Plt./214
(58) Field of Classification Search ..... Plt./214
See application file for complete search history.

*Primary Examiner*—Annette H Para
*Assistant Examiner*—Georgia Helmer
(74) *Attorney, Agent, or Firm*—C. A. Whealy

(57) ABSTRACT

A new and distinct cultivar of Juniper plant named 'Hulsdonk Yellow', characterized by its semi-dwarf and pyramidal plant form; yellow and dark green-colored leaves; and winter hardiness.

2 Drawing Sheets

Botanical designation: *Juniperus pingii.*
Cultivar denomination: 'Hulsdonk Yellow'.

BACKGROUND OF THE INVENTION

The present Invention relates to a new and distinct cultivar of Juniper, botanically known as *Juniperus pingii,* and hereinafter referred to by the name 'Hulsdonk Yellow'.

The new Juniper is a naturally-occurring branch mutation of *Juniperus pingii* 'Loderi', not patented. The new Juniper was discovered and selected by the Inventor from within a population of plants of 'Loderi' in a controlled greenhouse environment in Deurne, The Netherlands in 2000.

Asexual reproduction of the new Juniper by cuttings in a controlled greenhouse environment in Deurne, The Netherlands since 2000, has shown that the unique features of this new Juniper are stable and reproduced true to type in successive generations.

SUMMARY OF THE INVENTION

Plants of the cultivar Hulsdonk Yellow have not been observed under all possible environmental conditions. The phenotype may vary somewhat with variations in environment and culture such as temperature and light intensity without, however, any variance in genotype.

The following traits have been repeatedly observed and are determined to be the unique characteristics of the new Juniper. These characteristics in combination distinguish 'Hulsdonk Yellow' as a new and distinct cultivar of Juniper:

1. Semi-dwarf and pyramidal plant form.
2. Yellow and dark green-colored leaves.
3. Winter hardy.

Plants of the new Juniper are most similar to plants of the parent, 'Loderi'. Plants of the new Juniper differ from plants of 'Loderi' in the following characteristics:

1. Plants of the new Juniper are more compact than plants of 'Loderi'.
2. Plants of the new Juniper grow slower than plants of 'Loderi'.
3. Plants of the new Juniper and 'Loderi' differ in leaf color as plants of 'Loderi' have green-colored leaves.

Plants of the new Juniper can also be compared to plants of *Juniperus pingii* 'Glassell', not patented. Plants of the new Juniper differ from plants of 'Glassell' in the following characteristics:

1. Plants of the new Juniper are more uniform than plants of 'Glassell'.
2. Plants of the new Juniper and 'Glassell' differ in leaf color as plants of 'Glassell' have green-colored leaves.

BRIEF DESCRIPTION OF THE PHOTOGRAPHS

The accompanying colored photographs illustrate the overall appearance of the new Juniper, showing the colors as true as it is reasonably possible to obtain in colored reproductions of this type. Colors in the photographs may differ slightly from the color values cited in the detailed botanical description which accurately describe the colors of the new Juniper.

The photograph on the first sheet is a side perspective view of a typical plant of 'Hulsdonk Yellow' grown in a container.

The photograph on the second sheet is a close-up view of the foliage of a typical plant of 'Hulsdonk Yellow'.

DETAILED BOTANICAL DESCRIPTION

Plants used for the aforementioned photographs and following observations and measurements were grown in Deurne, The Netherlands during the summer and early autumn in an outdoor nursery and under conditions which approximate commercial Juniper production. During the production of the plants, day temperatures ranged from 10° C. to 28° C. and night temperatures ranged from 4° C. to 15° C. Plants had been growing for four years when the photographs and description were taken. In the following description, color references are made to The Royal Horticultural Society Colour Chart, 2001 Edition, except where general terms of ordinary dictionary significance are used.

Botanical classification:
*Juniperus pingii* 'Hulsdonk Yellow'.

Parentage:

Naturally-occurring branch mutation of *Juniperus pingii* 'Loderi', not patented.

Propagation:

*Type.*—By cuttings.

*Time to initiate roots.*—About three months at 15° C. to 25° C.

*Time to produce a rooted cutting.*—About 250 days at 15° C. to 25C.

*Root description.*—Fibrous, fleshy; white to brown in color.

*Rooting habit.*—Moderate branching; moderately dense.

Plant description:

*Form/growth habit.*—Semi-dwarf and pyramidal perennial evergreen shrub; upright to outwardly spreading plant habit. Low vigor.

*Branching habit.*—Freely branching with about 50 lateral branches developing per plant. Branches mostly upright. Plants maintain their lower branches and foliage at the soil level.

*Plant height.*—About 31.8 cm.

*Plant diameter.*—About 28.3 cm.

*Lateral branch description.*—Length: About 15.7 cm. Diameter: About 4 mm. Internode length: About 6 mm. Texture: Smooth, scaly. Strength: Strong. Color, developing: Close to 144A to 144C. Color, mature: Close to 200D.

*Leaf description.*—Appearance/arrangement: Flattened and appressed; opposite; sessile. Length: About 5 mm. Width: About 1.2 mm. Shape: Lanceolate, scale-like. Apex: Acute. Base: Cuneate. Margin: Entire. Texture, upper and lower surface: Smooth, glabrous. Venation pattern: Linear. Fragrance: Juniper-like. Color: Developing leaves, upper surface: Close to 157D. Developing leaves, lower surface: Between 1C to 2C. Fully expanded leaves, upper surface: Close to N155A; venation, similar to lamina. Fully expanded leaves, lower surface: Close to 137B; venation, similar to lamina.

*Cone description.*—Cone development has not been observed.

Disease/pest resistance: Plants of the new Juniper have not been noted to be resistant to pathogens or pests common to Juniper.

Weather tolerance: Plants of the new Juniper have been observed to be tolerant to drought, rain, wind and temperatures ranging from about −17° C. to about 35° C.

It is claimed:

1. A new and distinct Juniper plant named 'Hulsdonk Yellow' as illustrated and described.

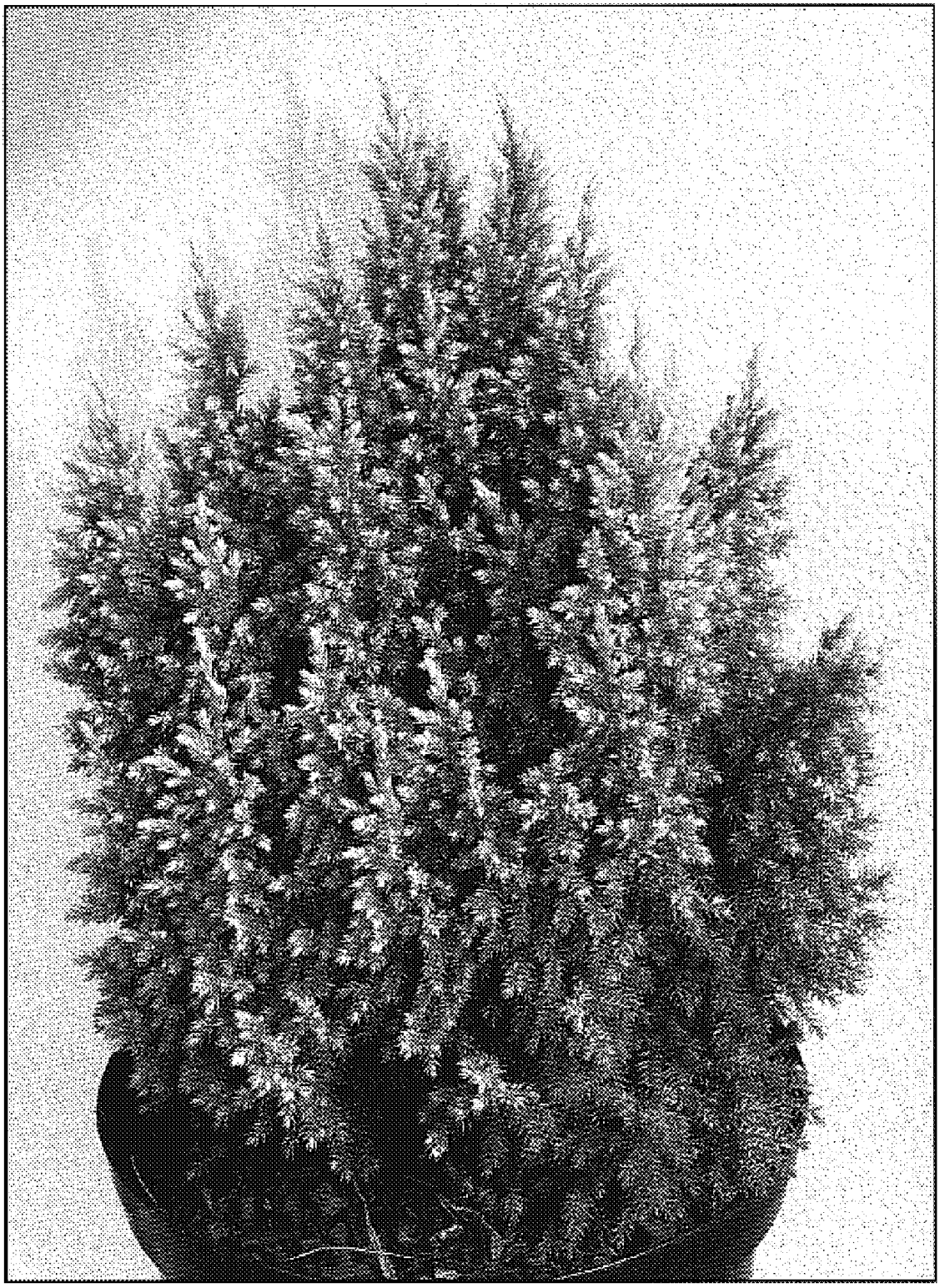

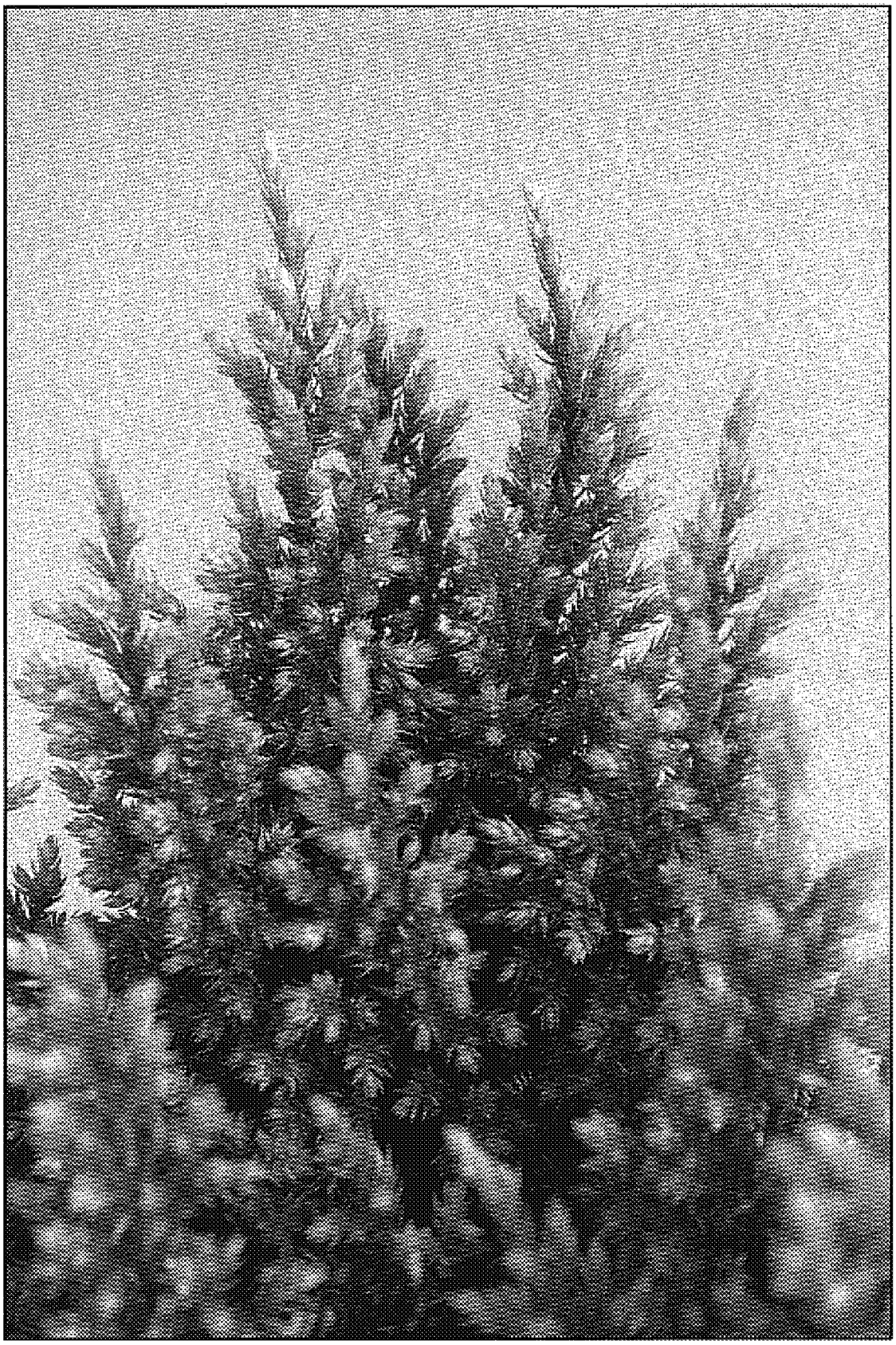

* * * * *